United States Patent [19]
Arcan et al.

[11] Patent Number: 5,916,160
[45] Date of Patent: Jun. 29, 1999

[54] REAL-TIME IMAGING CONTACT GAUGE AND VISUAL FEEDBACK INTERACTIVE APPARATUS INCLUDING SAME

[76] Inventors: Mircea Arcan, 42/22 Tagore, Tel Aviv 69341, Israel; Radu Arcan, 609 Old Country Rd., Elmsford, N.Y. 10523

[21] Appl. No.: 08/629,515

[22] Filed: Apr. 9, 1996

[51] Int. Cl.[6] ....................................... A61B 5/00
[52] U.S. Cl. ................... 600/407; 356/32; 73/762
[58] Field of Search ............... 600/407; 73/762, 73/865.4, 866.3, 379.02, 379.04, 502; 356/32, 33, 35

[56] References Cited

U.S. PATENT DOCUMENTS

| | | |
|---|---|---|
| 3,966,326 | 6/1976 | Brull et al. . |
| 4,501,159 | 2/1985 | Arcan . |
| 4,926,866 | 5/1990 | Lee . |
| 5,524,636 | 6/1996 | Sarvazyan et al. . |

OTHER PUBLICATIONS

Flexilite Brochure by Comlite B.V., no date.

*Primary Examiner*—Marvin M. Lateef
*Assistant Examiner*—Shawna J Shaw
*Attorney, Agent, or Firm*—Mark M. Friedman

[57] ABSTRACT

A real-time imaging contact gauge for indicating the distribution of contact pressure over a surface includes a transparent base panel, a pressure-transmitting member at one face of the transparent base panel for receiving the contact pressure to be indicated, a birefringent member sensitive to mechanical pressure located between the pressure-transmitting member and the transparent base panel, a plurality of spaced, parallel electro-luminescent layers carried by the transparent base panel for illuminating the birefringent layer, and a polarizer for polarizing the light transmitted to the birefringent layer to produce optical interference patterns corresponding to the contact presssure distribution applied to the pressure-transmitting member, which patterns are viewable through the opposite face of the transparent base panel.

7 Claims, 3 Drawing Sheets

REAL-TIME IMAGING CONTACT GAUGE AND VISUAL FEEDBACK INTERACTIVE APPARATUS INCLUDING SAME

FIELD AND BACKGROUND OF THE INVENTION

The present invention relates to a real-time, imaging contact gauge for indicating contact pressure distribution over a plane or curved surface, and also to a visual feedback interactive apparatus including such contact gauges.

Contact pressure distribution measurements are generally made by electronic or mechanical pressure transducers. However, such transducers are typically large and bulky; and even when they are miniaturized, it is still difficult to adapt them for use in a limited space because of their electrical and mechanical connections. In addition, the mere introduction of the transducers produces local stiffness changes in the contact surface which may affect the measurements. Further, using the known electronic and mechanical pressure transducers for indicating contact pressure distribution over a large surface generally involves a scanning process, and therefore does not permit simultaneous measurement of the pressure distribution over the complete surface. Still further, such known systems generally are very costly to produce and require a high level of technical personnel to operate and maintain them.

U.S. Pat. No. 3,966,326, of which one of the joint inventors of the present invention was also a joint inventor, disclosed a method and apparatus for indicating or measuring contact stress distribution over a surface by the use of a photoelastic (i.e., a birefringent) material having optical properties which are changed when the member is subjected to mechanical pressure. Photoelastic (birefringent) sheets had previously been used for indicating or measuring stresses on the outer areas of parts and structures manifested by the changes in the index of refraction of such materials when subjected to stresses. Thus, a polarized light wave passing through the stressed material splits into two separate light waves, each vibrating along a principal stress direction, and each travelling at a different speed. A "phase shift" between the two light waves is produced by the stresses, resulting in the production of an optical interference pattern which can be displayed and recorded. When such a stress sensitive material is subjected to in-plane strains and is viewed under polarized light, the resulting stresses are seen as colored interference patterns which can be interpreted to indicate the overall stress distribution and to provide accurate measurements of the stress directions and magnitudes.

Previous to the above-cited U.S. Pat. No. 3,966,326, photoelastic sheets had been used only for measuring in-plane stresses, i.e., stresses produced in the material by forces substantially coplanar to the sheet itself. The invention described in the above patent provided means, namely a pressure-transmitting member including a plurality of point-projections, which were effective to transmit the contact pressure in the form of a plurality of localized points to the photoelastic (birefringent) member, thereby converting the pressures perpendicular to the material into "in-plane" stresses coplanar to the material.

OBJECTS AND BRIEF SUMMARY OF THE INVENTION

An object of the present invention is to provide a novel real-time strip-like imaging contact gauge for indicating contact pressure distribution having significant advantages over the device of the above-cited patent. Another object of the present invention is to provide a visual feedback interactive apparatus including a real-time imaging contact gauge.

According to one aspect of the present invention, there is provided a real-time imaging contact gauge for indicating the distribution of contact pressure over a surface, comprising: a transparent base panel; a pressure-transmitting member at one face of the transparent base panel for receiving the contact pressure to be indicated; a birefringent member sensitive to mechanical pressure located between the pressure-transmitting member and the transparent base panel; a plurality of spaced, parallel electro-luminescent layers carried by the transparent base panel for illuminating the birefringent layer; and polarizer means for polarizing the light transmitted from the birefringent layer to produce optical interference patterns corresponding to the contact presssure distribution applied to the pressure-transmitting member, which patterns are viewable through the opposite face of the transparent base panel.

According to further features in the described preferred embodiments, the polarizer means includes a polarizer layer on one side of the birefringent member, and a reflector coating on the opposite side of the birefringent member.

It will thus be seen that such a real-time imaging contact gauge can be constructed as a self-contained unit to include its own light source. Moreover, it may be built in a very compact form as individual linear or curved strips and applied to various types of plane or curved surfaces of a wide variety of shapes and dimensions for indicating or measuring the contact stress distribution when applied to such surfaces.

According to another aspect of the present invention, there is provided a visual feedback interactive apparatus for displaying to a subject the contact pressure distribution of a body part of a subject received on a supporting surface, comprising: a supporting member including the supporting surface for receiving the body part of the subject; a real-time imaging contact gauge for indicating contact pressure distribution over the supporting surface, when the subject's body part is applied thereto, by producing optical interference patterns according to the distribution of the contact pressure applied over the supporting surface; an electronic camera for viewing the optical interference patterns and for converting them to electrical signals; and a TV or computer monitor viewable by the subject for receiving the electrical signals and for converting them to optical displays.

Such an apparatus may therefore serve as visual biofeedback instrumentation to enable a subject to instantly view the pressure distribution resulting from various muscle activities, and thereby to follow such activities and to take immediate corrective action if necessary. The apparatus would therefore be particularly useful to enable a person whose physical movements have been impaired, e.g., as a result of a stroke or an accident, to be trained to reinstate muscle control, body balance, etc.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figures 1, 2:
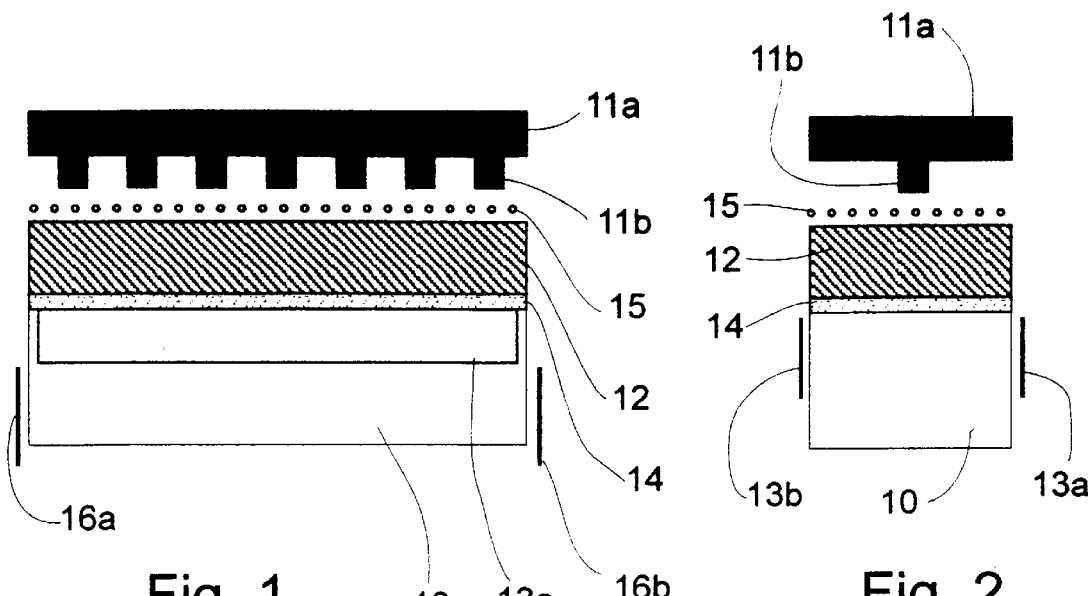
FIG. 1 is a lateral view.
FIG. 2 is a transverse sectional view, illustrating one form of real-time imaging contact gauge constructed in accordance with the present invention.

The real-time imaging contact gauge of FIGS. 1 and 2 includes a stiff transparent base panel, generally designated 10, carrying on its upper face a pressure-transmitting member 11 for receiving the contact pressure to be indicated or measured, and for transmitting it to a birefringent member 12 in the form of a layer sensitive to mechanical pressure.

The birefringent layer 12 is illuminated by an electroluminescent layer carried by the transparent base panel. In the example illustrated in FIGS. 1 and 2, there are two of said electro-luminescent layers 13a, 13b extending longitudinally on the two opposite sides of the transparent base panel 10, and extending longitudinally along the length of that panel, and two further electro-luminescent layers 16a, 16b on the above two opposite sides of the panel extending transversely across the width of the panel, such as to illuminate the birefringent layer 12 by directing light to and through the transparent base panel.

The illustrated contact gauge further includes polarizer means for polarizing the light transmitted from the birefringent layer 12. In the example of FIGS. 1 and 2, such polarizer means includes a circular polarizer layer on one side of the birefringent layer 12, and a reflector on the opposite side of that layer. Thus, the polarizer means shown in FIGS. 1 and 2 includes a circular polarizer (LH or RH) layer 14 between the birefringent layer 12 and the transparent base panel 10, and a reflector layer 15 between the birefringent layer 12 and the pressure-transmitting member 11.

The pressure-transmitting member 11 includes a planar strip 11a integrally formed with a plurality of projections 11b on its underface, facing the reflector layer 15 and the birefringent layer 12. Thus, as pressure is applied to the upper face of the planar strip 11a (e.g., by a person sitting or standing on it), this pressure is transmitted by the projections 11b and reflector layer 15 to the birefringent layer 12 where it is converted to in-plane stresses in that layer.

The contact gauge illustrated in FIGS. 1 and 2 operates as follows:

The two electro-luminescent layers 13a, 13b and 16a, 16b on the opposite sides of the transparent base panel 10 generate and direct light through that panel parallel to its plane. This light passes through the polarizer layer and through the birefringent layer 12, whereupon it is reflected by reflector layer 15 back through the birefringent layer 12 and the polarizer layer 14 through the transparent base panel 10 such that the light can be viewed from the face of panel 10 opposite to that facing the birefringent layer 12.

Pressure applied to the pressure-transmitting member 11 is converted to in-plane stresses in the birefringent layer 12, such that the polarized light passing through that layer produces an optical interference pattern which can be viewed from the outer surface of the transparent base panel 10. Thus, when the transparent base panel 10 is viewed via its face opposite to that of the birefringent layer 12, the resulting stresses are seen as colored interference patterns which can be interpreted to indicate the overall stress distribution and to provide accurate measurements of the contact stress magnitudes.

The electro-luminescent layers 13a, 13b may be, e.g., electro-luminescent foils available from Comlite Ltd., Haifa, Israel. The birefringent member 12 is preferably a cast obtained from mixing epoxy resins CY 208 and Araldite F with the hardener HY 956, available from Ciba Geigy. The reflector layer 15 is preferably an aluminum coating sprayed onto the respective surface of the birefringent layer 12. The result is an integrated structure wherein the birefringent layer 12 is integrated with the other layers 14, 15. Such an integrated structure has been found to produce a much finer, and more accurate, interference pattern than a loose optical sandwich as previously used.

Pressure-transmitting member 11 is preferably made of stiff rubber integrally formed with both the planar strip 11a and the projections 11b projecting from the underface of the strip.

Figures 1A, 2A:
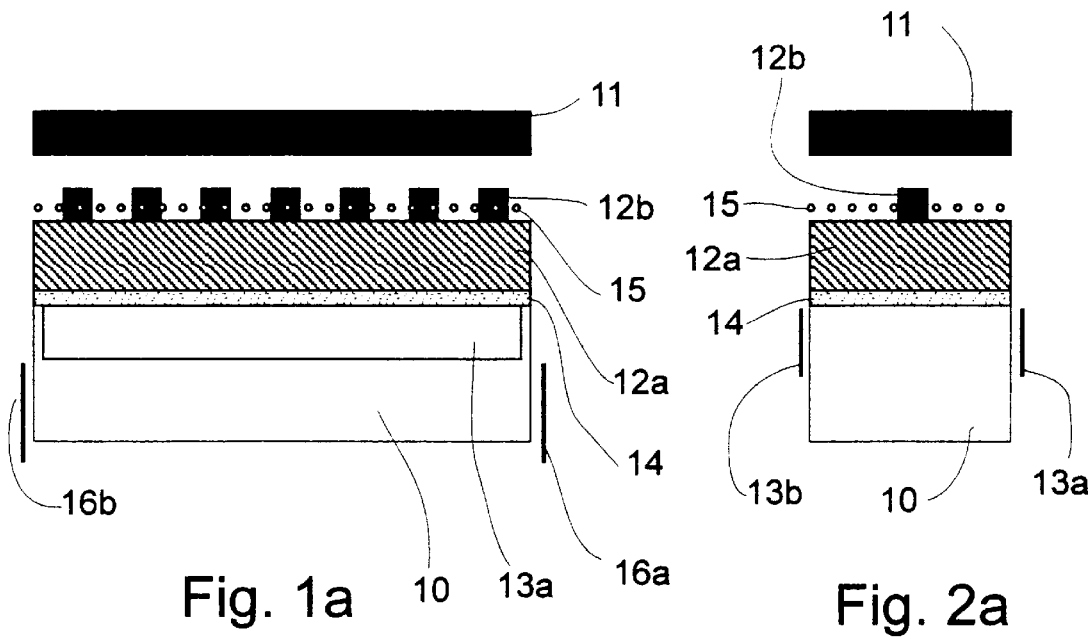
FIGS. 1a and 2a are views corresponding to those of FIGS. 1 and 2 but illustrating a modification in the construction of the gauge.

FIGS. 1a and 2a illustrate the same construction as FIGS. 1 and 2, respectively, except that the projections, 11b in FIGS. 1 and 2, are not formed on the pressure-transmitting member, but rather are cast together and are of the same material as the birefringent member or layer 12, wherein they are indicated as 12b. In all other respects, the construction and operation of the gauge illustrated in FIGS. 1a and 2a are the same as described above with respect to FIGS. 1 and 2.

Figure 3:
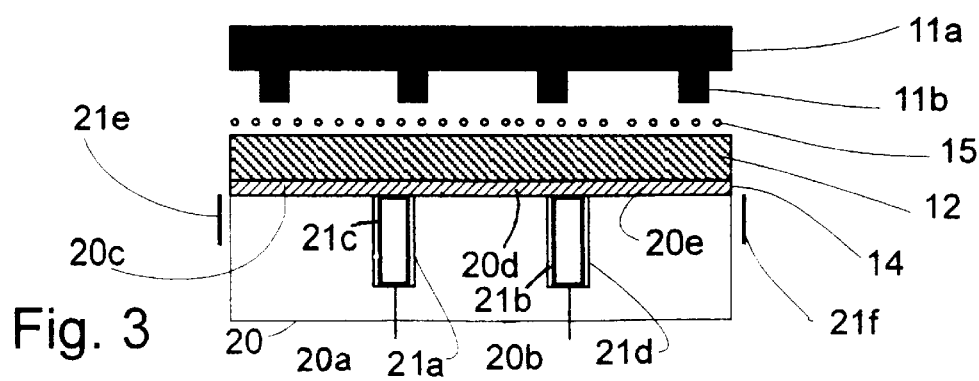
FIG. 3 is a sectional view illustrating a multiple contact gauge constructed according to FIGS. 1 and 2.

FIG. 3 illustrates the manner in which the contact gauge construction of FIGS. 1 and 2 (or FIGS. 1a and 2a) may be embodied in a large-area contact gauge, such as to cover the seat of a chair or the like. For this purpose, the transparent base panel, therein designated 20, is formed with a plurality of spaced parallel slots 20a, 20b defining a plurality of illuminated portions 20c, 20d, 20e of the transparent base panel between each pair of slots. Each of the illuminated portions of the transparent base panel is illuminated by a pair of electro-luminescent layers carried on the surfaces of the parallel slots on opposite sides of the respective illuminated portion of the transparent base panel. Thus, as shown in FIG. 3, the middle illuminated portion 20d of the transparent base panel 20 is illuminated by electro-luminescent layers 21a, 21b, on opposite sides of the transparent panel.

The upper surface of the transparent base panel 20 is covered by polarizer layer 14, birefringent layer 12, and reflector layer 15, corresponding to layers 14, 12 and 15, respectively, in FIGS. 1 and 2. These layers may be continuous layers covering the complete upper surface of the transparent base panel 20; alternatively, particularly when used with respect to curved surfaces, they could cover only the respective illuminated portions 20c, 20d, 20e of the panel.

A pressure-transmitting member constituted of elements 11a and 11b, corresponding to member 11 in FIGS. 1 and 2, is applied over all the foregoing layers on the illuminated portions 20c, 20d and 20e of the transparent base panel 20. Pressure-transmitting member 11 is of similar construction as described above with respect to member 11, including a planar strip integrally formed with a plurality of parallel, spaced projections extending along the length of the strip for transmitting the pressure stresses, via the reflector layer 15, to the birefringent layer 12.

The contact gauge illustrated in FIG. 3 is otherwise constructed and operates in the same manner as described above with respect to FIGS. 1 and 2. It is preferably used where the contact pressure to be indicated is distributed over a relatively large plane or curved area.

In all the foregoing constructions, the pressure-transmitting projections are in the form of a single linear rib, or a plurality of parallel, spaced linear ribs. However, they could also be in the form of spaced points, such as relatively sharp points, flat points (e.g., flat ends formed by cylindrical projections), or rounded points (e.g., rounded ends of semi-spherical projections).

Figure 4:
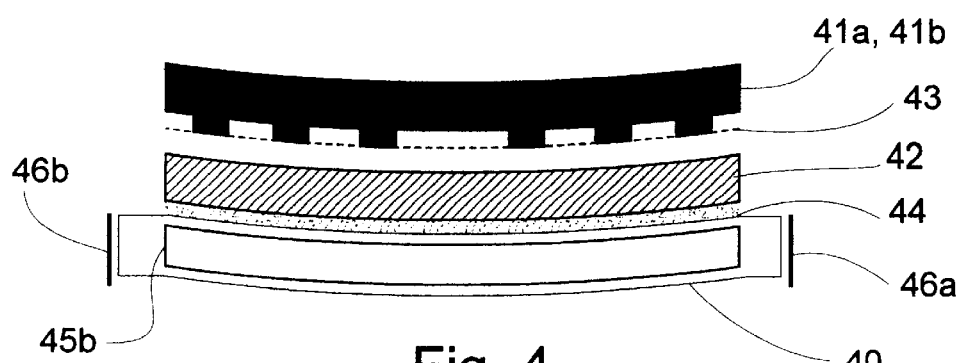
FIG. 4 is a lateral view illustrating a still further form of real-time imaging contact gauge constructed in accordance with the present invention for incorporation into the sitting area of a chair, for example.
Figure 5:
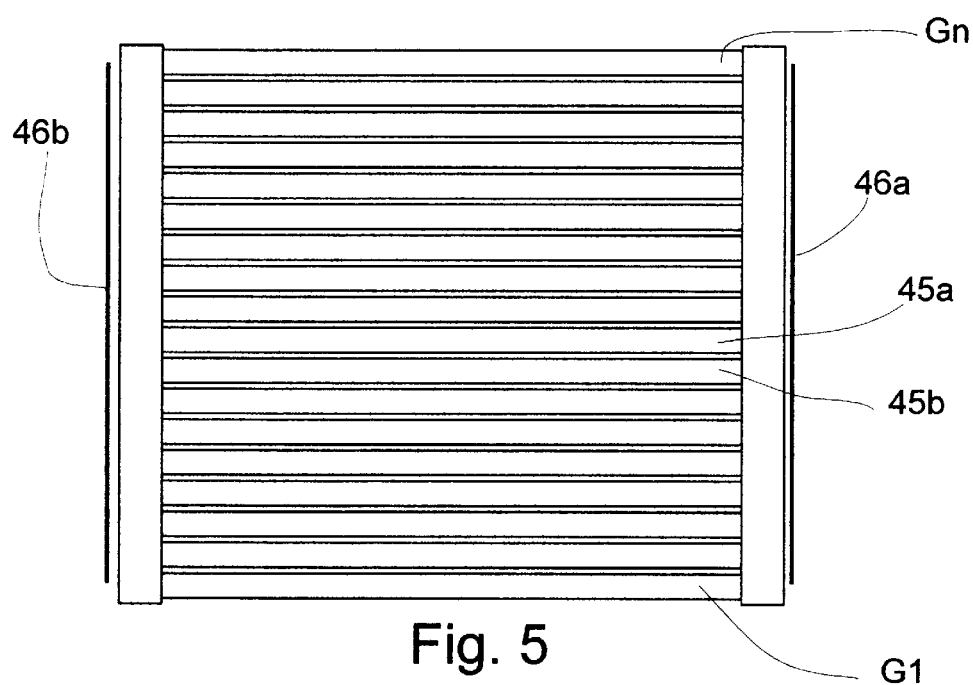
FIG. 5 is a top plan view of the gauge of FIG. 4.

FIGS. 4 and 5 illustrate a real-time imaging contact gauge similar to those described above but constructed to indicate the contact pressure distribution over a relatively large surface, such as over the seating area of a chair. In this example, the transparent base panel, therein generally designated 40, is of a large surface area and may be curved, as shown in FIG. 4, to conform to the curvature of the chair seat. The transparent base panel 40 supports the optical sandwich which includes the pressure-transmitting member 41. Member 41 is of a surface area corresponding to that of the transparent base panel 40 and is constructed as described above with respect to members 11a and 11b, including a layer 41a integrally formed on its underface with a plurality of spaced projections 41b. The upper surface of the transparent base panel 40 is covered by a circular polarizer layer 44, by a birefringent layer 42, and by a reflector layer 43. The gauge is constructed in the form of strips such that a plurality of such gauges $G_1$–$G_n$ may be applied to cover a large surface area. For illumination, electroluminescent sheets 45a and 45b may straddle the opposite sides of each gauge $G_1$–$G_n$, and/or electroluminescent sheets 46a and 46b may extend transversely across the opposite ends of all the gauges.

Figure 6:
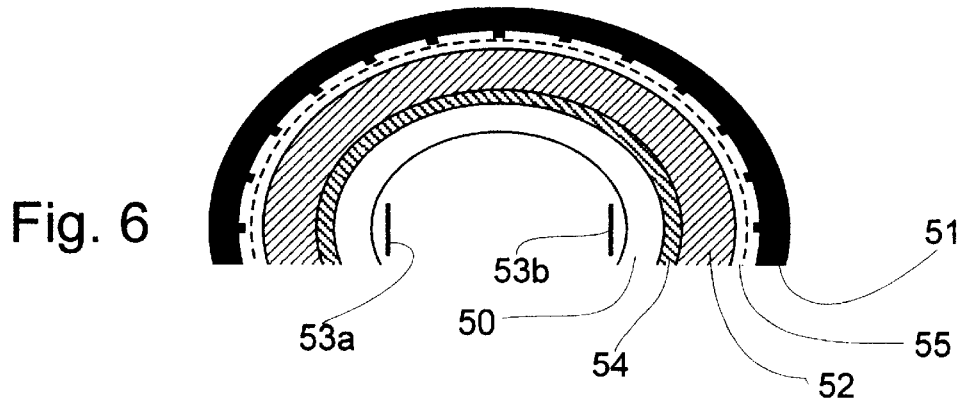
FIG. 6 is a lateral view illustrating a further real-time imaging contact gauge constructed in accordance with the present invention for incorporating, for example, in a hand or finger exerciser.
Figure 7:
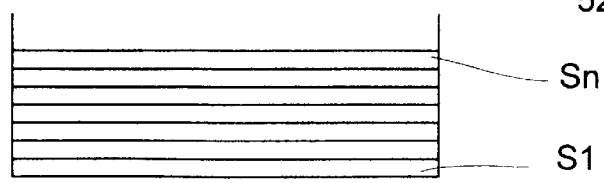
FIG. 7 is a top plan view of the gauge of FIG. 6.

FIGS. 6 and 7 illustrate a real-time imaging contact gauge system for indicating contact pressure distribution over a relatively large surface for use as a hand-grip or finger exerciser. The construction of the gauge in FIGS. 6 and 7 includes a transparent base panel 50 of curved configuration, illuminated by electro-luminescent sheets-53a, 53b on its opposite faces to direct the light parallel to the transparent base panel. The pressure-transmitting member 51 is of a similar curved configuration as the transparent base panel 50 and is constructed with the spaced projections described previously. The user engages the outer surface of the pressure-transmitting member 51, and the pressure stresses applied thereto are viewable through the inner face of the transparent base panel 50. In addition, the real-time imaging gauge includes a reflector layer 55, a birefringent layer 52, and a circularly polarizer layer 54, in that order, according to the construction illustrated in FIG. 6. As shown in FIG. 7, each gauge is constructed in the form of a strip, a plurality of such strips $S_1$–$S_n$ being used for measuring the large surface area grasped by the user's hand.

Figure 8:
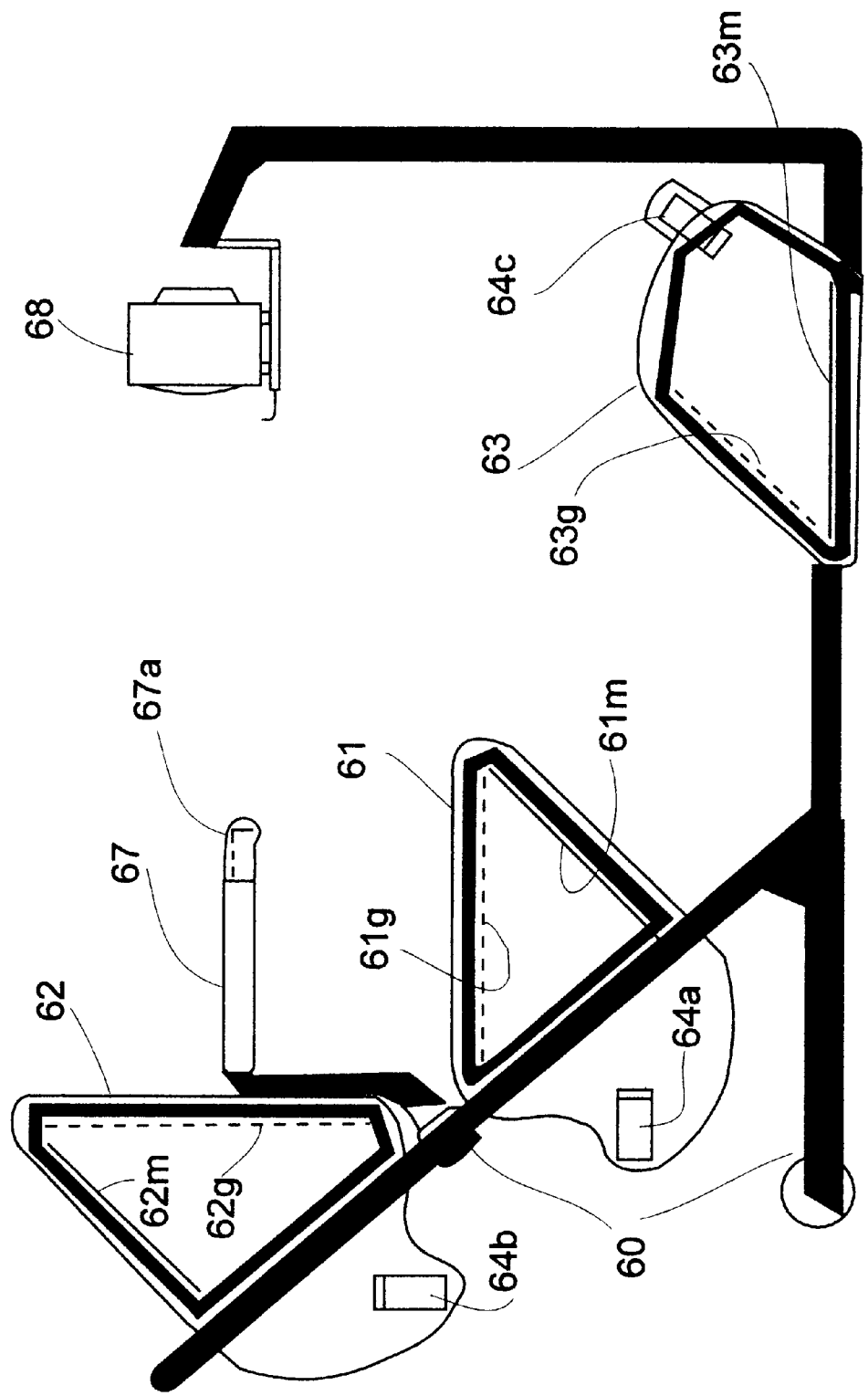
FIG. 8 illustrates one form of visual feedback interactive apparatus (a chair) including a plurality of real-time imaging contact gauges constructed in accordance with the present invention for visually indicating the contact pressure distribution over various body parts of the subject.

FIG. 8 illustrates one form of visual feedback apparatus which may be constructed to include the real-time imaging contact gauges described above. Thus, the apparatus illustrated in FIG. 8 includes a seat imaging box 61, backrest imaging box 62, and footrest imaging box 63. Each of the imaging boxes 61, 62, 63 includes a real-time imaging contact gauge system 61g, 62g, 63g, respectively, e.g., as described above with respect to FIGS. 3–5. Each of the gauge systems may generate its own light such that the interference patterns produced by the pressure stresses are converted to interference patterns viewable through the side of the transparent base panel in the respective gauge opposite to that receiving the pressure.

The apparatus illustrated in FIG. 8 further includes three electronic cameras 64a, 64b, 64c adapted to view the optical interference patterns from the three contact gauge systems 61g, 62g and 63g, respectively. Preferably all the gauge systems are viewed via 45° mirrors, as shown at 61m, 62m and 63m, respectively.

The armrest 67 may be similarly equipped with a handgrip gauge 67a, and may be rotatable so as to to enable the produced interference patterns to be directly viewed by the subject. A TV or computer monitor 68 faces the subject so that it can be viewed by the subject.

Thus, as the subject sits on seat 61, the subject's back may be pressed against backrest 62, feet against footrest 63, and handgrip against armrest 67. The pressure distributions in these elements of the chair are either directly observed, viewed by cameras 64a, 64b, 64c and converted to electrical signals transmitted to the monitor 68 for display and for being observed by the subject. Thus, the pressure distributions are converted to optical images which can be viewed in a real-time manner by the subject. This permits the subject to see the pressure distribution in the various body parts and to take whatever corrective action may be appropriate for the particular situation to reinstate muscle control, body balance, etc., during physical therapy treatment.

The illustrated apparatus thus provides real-time contact pressure imaging and visual feedback to a subject, permitting the subject to understand and follow the subject's muscle activities and to learn again, after a stroke or an accident, to govern motor abilities.

While the invention has been described with respect to several preferred embodiments, it will be appreciated that these are set forth merely for purposes of example, and that many other variations, modifications and applications of the invention may be made.

We claim:

1. Visual feedback interactive system for displaying to a subject the contact distribution of a body part of the subject received on a supporting surface, comprising:

a plurality of imaging boxes each box comprising:

(a) a supporting member including said supporting surface for receiving said body part of the subject;

(b) a real-time imaging contact gauge for indicating contact pressure distribution over said supporting surface by producing optical interference patterns according to the distribution of the contact pressure applied over said supporting surface; and (c) an electronic camera for viewing said optical interference patterns and for converting them to electrical signals; and a monitor viewable in real-time by the subject for receiving said electrical signals and for converting them to optical displays so that the subject views the contact distribution of said body part on said supporting surface to obtain visual feedback and take appropriate interactive corrective action of said body part to reinstate muscle control and body balance.

2. The apparatus according to claim 1, wherein said real-time imaging contact gauge comprises:
- a transparent base panel;
- a pressure-transmitting member at one face of the transparent base panel for receiving the contact pressure to be indicated;
- a birefringent layer sensitive to mechanical pressure located between the pressure-transmitting member and the transparent base panel;
- an electro-luminescent layer carried by the transparent base panel for illuminating said birefringent layer;
- and polarizer means for polarizing the light transmitted from the birefringent layer to produce optical interference patterns corresponding to the contact presssure distribution applied to said pressure-transmitting member, which patterns are viewable through the opposite face of the transparent base panel.

3. The apparatus according to claim 1, wherein said supporting member is a chair, and said supporting surface receiving said real-time imaging contact gauge is on the seat of the chair.

4. The apparatus according to claim 3, wherein said chair also includes a second supporting surface in the form of a backrest also receiving a real-time imaging contact gauge for indicating the contact pressure distribution over said backrest.

5. The apparatus according to claim 4, wherein said chair includes a further supporting surface in the form of a footrest, which footrest also receives a real-time imaging contact gauge for indicating the contact pressure distribution over said footrest.

6. The apparatus according to claim 1, wherein said supporting member is a foot analyzer enabling the subject's foot structure and movements to be analyzed.

7. The apparatus according to claim 1, wherein said supporting member is a hand-grip analyzer, enabling the subject's hand-grip movements to be analyzed.

* * * * *